US00PP23070P2

(12) United States Plant Patent
van Huylenbroeck

(10) Patent No.: US PP23,070 P2
(45) Date of Patent: Sep. 25, 2012

(54) ***HYDRANGEA* PLANT NAMED 'ILVOMINDY'**

(50) Latin Name: *Hydrangea paniculata*
Varietal Denomination: Ilvomindy

(75) Inventor: Johan van Huylenbroeck, Melle (BE)

(73) Assignee: Spring Meadow Nursery, Inc., Grand Haven, MI (US)

( * ) Notice: Subject to any disclaimer, the term of this patent is extended or adjusted under 35 U.S.C. 154(b) by 126 days.

(21) Appl. No.: 12/928,266

(22) Filed: Dec. 7, 2010

(51) Int. Cl.
*A01H 5/00* (2006.01)

(52) U.S. Cl. ..... Plt./250

(58) Field of Classification Search ..... Plt./250
See application file for complete search history.

(56) References Cited

OTHER PUBLICATIONS

Pluto Plant Variety Database, citation for *Hydrangea* 'Ilvomindy' retrieved on May 23, 2012. Retrieved from the Internet at <http://www.upov.int/pluto/en/> 2011, one page.*

* cited by examiner

*Primary Examiner* — June Hwu
(74) *Attorney, Agent, or Firm* — C. A. Whealy

(57) ABSTRACT

A new and distinct cultivar of *Hydrangea* plant named 'Ilvomindy', characterized by its upright and mounded plant habit; freely branching habit; freely flowering habit; strong and sturdy stems that hold inflorescences upright; and large conical inflorescences with numerous large white-colored sterile flowers that with development become greyed purple in color.

2 Drawing Sheets

Botanical designation: *Hydrangea paniculata.*
Cultivar denomination: 'ILVOMINDY'.

BACKGROUND OF THE INVENTION

The present invention relates to a new and distinct cultivar of *Hydrangea* plant, botanically known as *Hydrangea paniculata* and hereinafter referred to by the name 'Ilvomindy'.

The new *Hydrangea* plant is a product of a planned breeding program conducted by the Inventor in Melle, Belgium. The objective of the breeding program was to develop new compact and early flowering *Hydrangea* plants with strong stems and attractive flower coloration.

The new *Hydrangea* plant originated from an open-pollination during the summer of 2001 of the *Hydrangea paniculata* 'Pink Diamond', not patented, as the female, or seed parent and an unknown selection of *Hydrangea paniculata* as the male, or pollen, parent. The new *Hydrangea* plant was discovered and selected by the Inventor during the summer of 2003 as a single flowering plant from within the progeny of the stated open-pollination in a controlled environment in Melle, Belgium.

Asexual reproduction of the new cultivar by softwood cuttings in a controlled environment in Melle, Belgium since July, 2003 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environmental conditions such as temperature and light intensity without, however, any variance in genotype.

The following traits have been repeatedly observed and are determined to be the unique characteristics of 'Ilvomindy'.

These characteristics in combination distinguish 'Ilvomindy' as a new and distinct *Hydrangea* plant:

1. Upright and mounded plant habit.
2. Freely branching habit.
3. Freely flowering habit.
4. Strong and sturdy stems that hold inflorescences upright.
5. Large conical inflorescences with numerous large white-colored sterile flowers that with development become greyed purple in color.

Plants of the new *Hydrangea* differ from plants of the female parent, 'Pink Diamond', in the following characteristics:

1. Inflorescences of plants of the new *Hydrangea* have more rounded apices than inflorescences of plants of 'Pink Diamond'.
2. Plants of the new *Hydrangea* have smaller sterile flowers than plants of 'Pink Diamond'.

Plants of the new *Hydrangea* can be compared to plants of *Hydrangea paniculata* 'DVP Pinky', disclosed in U.S. Plant Pat. No. 16,166. In side-by-side comparisons conducted in Grand Haven, Mich., plants of the new *Hydrangea* differed from plants of 'DVP Pinky' in the following characteristics:

1. Plants of the new *Hydrangea* were more vigorous than plants of 'DVP Pinky'.
2. Inflorescences of plants of the new *Hydrangea* had more rounded apices than inflorescences of plants of 'DVP Pinky'.
3. Plants of the new *Hydrangea* had larger sterile flowers than plants of 'DVP Pinky'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a close-up view of a typical flowering plant of 'Ilvomindy' in the autumn.

The photograph on the second sheet is a close-up view of typical sterile flowers of 'Ilvomindy' that are beginning to change color.

DETAILED BOTANICAL DESCRIPTION

Plants used for the aforementioned photographs and the following description were grown during the summer and autumn in an outdoor nursery in Grand Haven, Mich. and under conditions which closely approximate commercial *Hydrangea* production conditions. Plants of the new *Hydrangea* were three years old when the photographs and description were taken. In the following description, color references are made to The Royal Horticultural Society Colour Chart, 2001 Edition, except where general terms of ordinary dictionary significance are used.

Botanical description: *Hydrangea paniculata* 'Ilvomindy'.

Parentage:

*Female, or seed, parent.*—*Hydrangea paniculata* 'Pink Diamond', not patented.

*Male, or pollen, parent.*—Unknown selection of *Hydrangea paniculata*, not patented.

Propagation:

*Type cutting.*—By softwood cuttings.

*Time to initiate roots, summer.*—About 20 days at temperatures of about 20° C.

*Time to produce a rooted young plant, summer.*—About two months at temperatures of about 20° C.

*Root description.*—Fine and thick; creamy white in color.

*Rooting habit.*—Freely branching; dense.

Plant description:

*Plant form and growth habit.*—Perennial deciduous shrub; upright and mounded plant habit; broad inverted triangle; strong and sturdy lateral branches; freely branching habit with about 26 lateral branches developing per plant; vigorous growth habit.

*Plant height.*—About 100 cm to 130 cm.

*Plant diameter or area of spread.*—About 70 cm.

*Lateral branches.*—Length: About 60 cm. Diameter: About 6 mm. Internode length: About 4.5 cm. Texture: Smooth, glabrous. Strength: Strong, sturdy. Color, developing: Close to 166A. Color, developed: Close to 197A.

Foliage description:

*Arrangement.*—Opposite, simple.

*Length.*—About 11 cm.

*Width.*—About 4.2 cm.

*Shape.*—Elliptic to ovate.

*Apex.*—Acute.

*Base.*—Cuneate to attenuate.

*Margin.*—Serrate.

*Texture, upper surface.*—Slightly rugose, slightly pubescent.

*Texture, lower surface.*—Slightly rugose, glabrous.

*Venation pattern.*—Pinnate.

*Color.*—Developing leaves, upper and lower surfaces: Close to 144A. Fully expanded leaves, upper surface: Close to 147A; venation, close to 144A. Fully expanded leaves, lower surface: Close to 147B; venation, close to 144A.

*Petioles.*—Length: About 1 cm. Diameter: About 2 mm. Texture, upper and lower surfaces: Smooth, glabrous. Color, upper and lower surfaces: Close to 144A.

Flower description:

*Flower type and habit.*—Single sterile and fertile flowers arranged on large terminal conical panicles; flowers face upright to outwardly.

*Fragrance.*—None detected.

*Natural flowering season.*—Continuous flowering from July until October in Grand Haven, Mich.

*Flower longevity, fertile flowers.*—Flowers last about four weeks on the plant; flowers not persistent.

*Flower longevity, sterile flowers.*—Flowers last about four months on the plant; flowers persistent.

*Quantity of flowers.*—Freely flowering habit with about 236 fertile flowers and about 128 sterile flowers per inflorescence.

*Inflorescence height.*—About 25 cm.

*Inflorescence diameter.*—About 18 cm.

*Flower diameter, fertile flowers.*—About 6 mm.

*Flower depth (height), fertile flowers.*—About 5 mm.

*Flower diameter, sterile flowers.*—About 6.5 cm.

*Flower depth (height), sterile flowers.*—About 2 cm.

*Flower buds, fertile and sterile flowers.*—Length: About 4 mm. Diameter: About 3 mm. Shape: Elliptic. Color: Close to 155C.

*Petals, fertile flowers only.*—Arrangement: Five in a single whorl. Length: About 3 mm. Width: About 2 mm. Shape: Narrowly elliptic. Apex: Acute. Base: Attenuate. Margin: Entire. Texture, upper and lower surfaces: Smooth, glabrous. Color: When opening, upper and lower surfaces: Close to 155C. Fully opened, upper and lower surfaces: Close to 155C.

*Sepals, fertile flowers.*—Quantity per flower: Five in a single whorl. Length: About 0.5 mm. Width: About 0.5 mm. Shape: Ovate. Apex: Acute. Base: Fused. Margin: Entire. Texture, upper and lower surfaces: Smooth, glabrous. Color, upper and lower surfaces: Close to 145C.

*Sepals, sterile flowers.*—Quantity per flower: About four in a single whorl. Length: About 3 cm to 4 cm. Width: About 2 cm to 2.5 cm. Shape: Broadly elliptic to ovate. Apex: Broadly acute to rounded. Base: Obtuse. Margin: Entire. Texture, upper and lower surfaces: Smooth, glabrous. Color: When opening and fully opened, upper surface: Close to 155D; with development, color becoming closer to 62C and 148B and eventually closest to 184B. When opening and fully opened, lower surface: Close to 155D; with development, color becoming closer to 62C and 148B and eventually closest to 184B.

*Pedicels, fertile flowers.*—Angle: Erect to about 10° from vertical. Strength: Strong. Length: About 4 mm. Diameter: About 1 mm. Texture: Smooth, glabrous. Color: Close to 155C.

*Pedicels, sterile flowers.*—Angle: Erect to about 90° from vertical. Strength: Strong. Length: About 3 cm. Diameter: About 1.5 mm. Texture: Smooth, glabrous. Color: Close to 155C.

*Reproductive organs, fertile flowers only.*—Stamens: Quantity per flower: About five. Anther shape: Rounded. Anther length: About 0.5 mm. Anther color:

Close to 155C. Pollen amount: Scarce. Pollen color: Close to 155C. Pistils: Pistil quantity per flower: Three. Pistil length: About 0.5 mm. Stigma shape: Elliptic. Stigma color: Close to 155C. Style length: About 0.35 mm. Style color: Close to 155C. Ovary color: Close to 155A.

*Seeds*.—Quantity per inflorescence: Numerous. Size: Less than 0.1 mm by less than 0.1 mm. Color: Brown.

Disease/pest resistance: Plants of the new *Hydrangea* have not been observed to be resistant to pathogens or pests common to *Hydrangea*.

Temperature tolerance: Plants of the new *Hydrangea* have been shown to be tolerant to temperatures ranging from about −30° C. to about 38° C.

It is claimed:

1. A new and distinct *Hydrangea* plant named 'Ilvomindy' as illustrated and described.

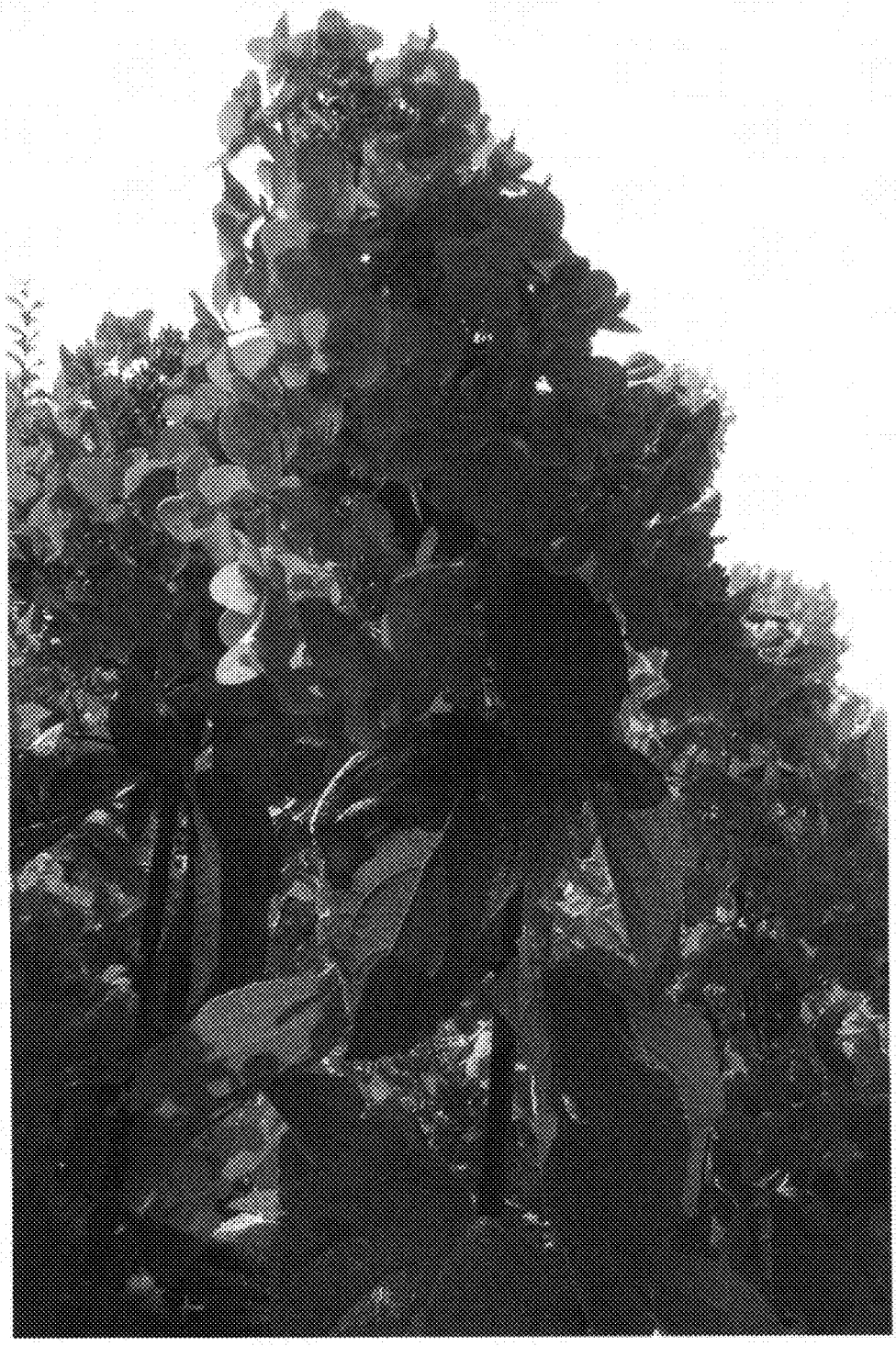

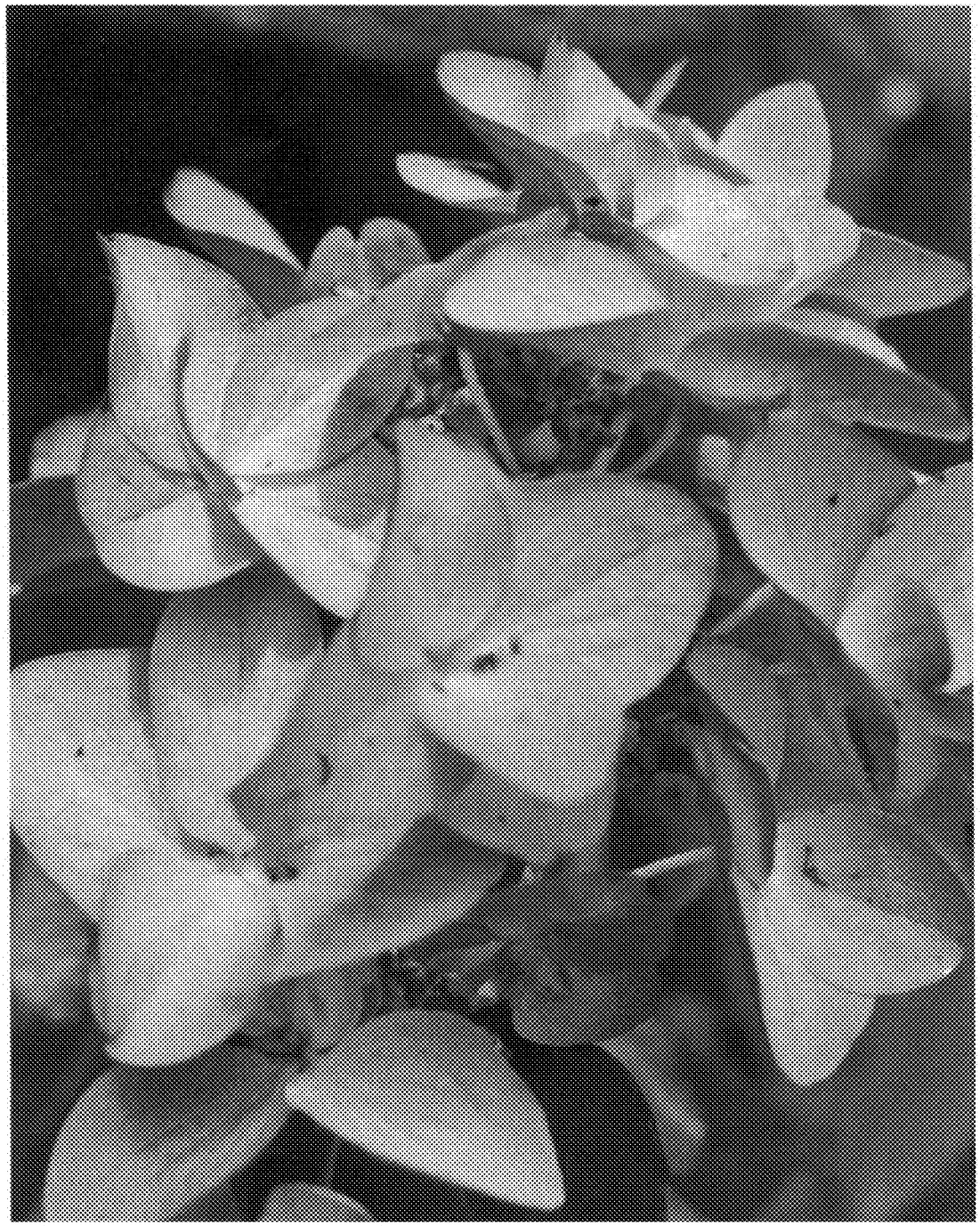

* * * * *